US010952683B2

(12) United States Patent
Jones et al.

(10) Patent No.: US 10,952,683 B2
(45) Date of Patent: Mar. 23, 2021

(54) METHOD AND APPARATUS FOR ESTIMATING BREATHING RATE

(71) Applicant: Oxehealth Limited, Oxford (GB)

(72) Inventors: Simon Mark Chave Jones, Oxford (GB); Nicholas Dunkley Hutchinson, Oxford (GB)

(73) Assignee: OXEHEALTH LIMITED, Oxford (GB)

( * ) Notice: Subject to any disclaimer, the term of this patent is extended or adjusted under 35 U.S.C. 154(b) by 0 days.

(21) Appl. No.: 16/071,570

(22) PCT Filed: Jan. 19, 2017

(86) PCT No.: PCT/GB2017/050128
§ 371 (c)(1),
(2) Date: Jul. 20, 2018

(87) PCT Pub. No.: WO2017/125744
PCT Pub. Date: Jul. 27, 2017

(65) Prior Publication Data
US 2019/0029604 A1    Jan. 31, 2019

(30) Foreign Application Priority Data
Jan. 21, 2016    (GB) .................................... 1601142

(51) Int. Cl.
*A61B 5/11*    (2006.01)
*A61B 5/00*    (2006.01)
(Continued)

(52) U.S. Cl.
CPC .......... *A61B 5/7278* (2013.01); *A61B 5/0077* (2013.01); *A61B 5/0816* (2013.01);
(Continued)

(58) Field of Classification Search
CPC ....... A61M 2016/0036; G02B 27/4227; G06F 16/7837
(Continued)

(56) References Cited

U.S. PATENT DOCUMENTS 10,034,979 B2    7/2018    Bechtel et al.
10,292,662 B2    5/2019    Kirenko
(Continued)

FOREIGN PATENT DOCUMENTS

EP    0919184 A1    6/1999
EP    2767233 A1    8/2014
(Continued)

OTHER PUBLICATIONS

International Search Report for PCT/GB2017/050128, ISA/EP, Rijswijk, NL, dated Apr. 13, 2017.
(Continued)

*Primary Examiner* — Kiet M Doan
(74) *Attorney, Agent, or Firm* — Harness, Dickey & Pierce, P.L.C.

(57) ABSTRACT

A method and apparatus for extracting a breathing rate estimate from video images of a respiring subject. Signals corresponding to the spatial coordinates of feature points tracked through the video sequence are filtered and excessively large changes are attenuated to reduce movement artefacts. The signals are differentiated and signals which correlate most strongly with other signals are selected. The selected signals are subject to principal component analysis and the best quality of the top five principal components is selected and its frequency is used to calculate and output a breathing rate estimate. The method is particularly suitable for detecting respiration in subject in secure rooms where
(Continued)

the video image is of substantially the whole room and the subject is only a small part of the image, and maybe covered or uncovered.

12 Claims, 9 Drawing Sheets

(51) Int. Cl.
  *A61B 5/113* (2006.01)
  *G06T 7/246* (2017.01)
  *A61B 5/08* (2006.01)
  *G06K 9/00* (2006.01)

(52) U.S. Cl.
  CPC .............. *A61B 5/113* (2013.01); *A61B 5/1114* (2013.01); *A61B 5/1128* (2013.01); *A61B 5/7221* (2013.01); *A61B 5/742* (2013.01); *G06K 9/00744* (2013.01); *G06T 7/246* (2017.01); *G06T 2207/10016* (2013.01); *G06T 2207/30004* (2013.01); *G06T 2207/30076* (2013.01); *G06T 2207/30196* (2013.01); *G06T 2207/30232* (2013.01)

(58) Field of Classification Search
  USPC ........... 345/633; 382/37, 103; 600/534, 301, 600/486
  See application file for complete search history.

(56) References Cited

U.S. PATENT DOCUMENTS

| | | |
|---|---|---|
| 2003/0228032 A1 | 12/2003 | Rui et al. |
| 2005/0197590 A1 | 9/2005 | Osorio et al. |
| 2006/0058618 A1 | 3/2006 | Nishiura |
| 2007/0156060 A1 | 7/2007 | Cervantes |
| 2007/0195931 A1 | 8/2007 | Ohishi |
| 2008/0292151 A1 | 11/2008 | Kurtz et al. |
| 2010/0049064 A1 | 2/2010 | Bodmer et al. |
| 2010/0074475 A1 | 3/2010 | Chouno |
| 2010/0298656 A1 | 11/2010 | McCombie et al. |
| 2011/0046498 A1 | 2/2011 | Klap et al. |
| 2011/0150274 A1 | 6/2011 | Patwardhan et al. |
| 2012/0141000 A1 | 6/2012 | Jeanne et al. |
| 2012/0213405 A1 | 8/2012 | Sasaki |
| 2014/0003690 A1 | 1/2014 | Razeto et al. |
| 2014/0037163 A1 | 2/2014 | Kirenko et al. |
| 2014/0037166 A1 | 2/2014 | De Haan et al. |
| 2014/0236036 A1* | 8/2014 | de Haan ............... A61B 5/1135 600/534 |
| 2014/0276104 A1 | 9/2014 | Tao et al. |
| 2014/0371635 A1 | 12/2014 | Shinar et al. |
| 2015/0208987 A1 | 7/2015 | Shan et al. |
| 2015/0363361 A1* | 12/2015 | Kniazev ............. G05B 23/0224 703/2 |
| 2016/0106340 A1 | 4/2016 | Mestha et al. |
| 2016/0125260 A1* | 5/2016 | Huang .................. G06K 9/4671 382/201 |
| 2016/0253820 A1 | 9/2016 | Jeanne et al. |
| 2017/0007185 A1 | 1/2017 | Lin et al. |
| 2017/0042432 A1* | 2/2017 | Adib ..................... G01S 13/536 |
| 2017/0224256 A1 | 8/2017 | Kirenko |
| 2017/0238805 A1 | 8/2017 | Addison et al. |
| 2017/0238842 A1 | 8/2017 | Jacquel et al. |
| 2018/0279885 A1 | 10/2018 | Bulut |
| 2019/0000391 A1 | 1/2019 | De Haan et al. |
| 2019/0267040 A1 | 8/2019 | Ikeda et al. |

FOREIGN PATENT DOCUMENTS

| | | |
|---|---|---|
| EP | 2988274 A2 | 2/2016 |
| WO | WO-2011021128 A2 | 2/2011 |
| WO | WO-2013027027 A2 | 2/2013 |
| WO | WO-2014131850 A1 | 9/2014 |
| WO | WO-2014140994 A1 | 9/2014 |
| WO | WO-201504915 A1 | 4/2015 |
| WO | WO-2015049150 A1 | 4/2015 |
| WO | WO-2015172735 A1 | 11/2015 |
| WO | WO-2016094749 A1 | 6/2016 |
| WO | WO-2017125744 A1 | 7/2017 |

OTHER PUBLICATIONS

Written Opinion of the ISA for PCT/GB2017/050128, ISA/EP, Rijswijk, NL, dated Apr. 13, 2017.
Search Report under Section 17(5) for priority application GB1601142. 1, UKIPO, Newport, South Wales, dated Jun. 28, 2016.
Verkruysse et al., "Remote Plethysmographic imaging using ambient light", Optics Express, 16(26), Dec. 22, 2008, pp. 21434-21445.
Tarassenko et al, "Non-contact video-based vital sign monitoring using ambient light and auto-regressive models", 2014 Physiol. Meas. 35 807, pp. 807-831.
Wu et al, Eulerian Video Magnification for Revealing Subtle Changes in the World, 2012.
Kumar-DistancePPG: Robust non-contact vital signs monitoring using a camera, Optical Society of America (2015).
Pisani-Real-time Automated Detection of Clonic Seizures in Newborns, Clinical Neurophysiology 125 (2014) 1533-1540.
European Search Report regarding Application No. EP 19 15 8085 dated Jul. 10, 2019.
Nakajima, Kazuki, Yoshiaki Matsumoto, and Toshiyo Tamura. "Development of real-time image sequence analysis for evaluating posture change and respiratory rate of a subject in bed." Physiological Measurement 22.3 (2001).
Search Report of UKIPO regarding Application No. GB1900033.0 dated Jun. 13, 2019.
British Search Report regarding Appliction No. 1900034.8 dated Jun. 13, 2019.
Extended EP Search Report regarding Application No. 19220090.5 dated Feb. 24, 2020.
U.S. Appl. No. 16/732,769, filed Jan. 2, 2020, Nicholas Dunkley Hutchinson.
U.S. Appl. No. 16/732,979, filed Jan. 2, 2020, Nicholas Dunkley Hutchinson.
U.S. Appl. No. 16/733,065, filed Jan. 2, 2020, Nicholas Dunkley Hutchinson.
U.S. Appl. No. 15/961,279, filed Apr. 24, 2018, Nicholas Dunkley Hutchinson.
U.S. Appl. No. 16/071,542, filed Jul. 20, 2018, Nicholas Dunkley Hutchinson.
U.S. Appl. No. 16/071,591, filed Jul. 20, 2018, Muhammad Fraz.
U.S. Appl. No. 16/071,611, filed Jul. 20, 2018, Nicholas Dunkley Hutchinson.
U.S. Appl. No. 16/291,728, filed Mar. 4, 2019, Nicholas Dunkley Hutchinson.
U.S. Appl. No. 16/334,211, filed Mar. 18, 2019, Mohamed Elmikaty.
U.S. Appl. No. 16/347,925, filed May 7, 2019, Simon Mark Chave Jones.

* cited by examiner

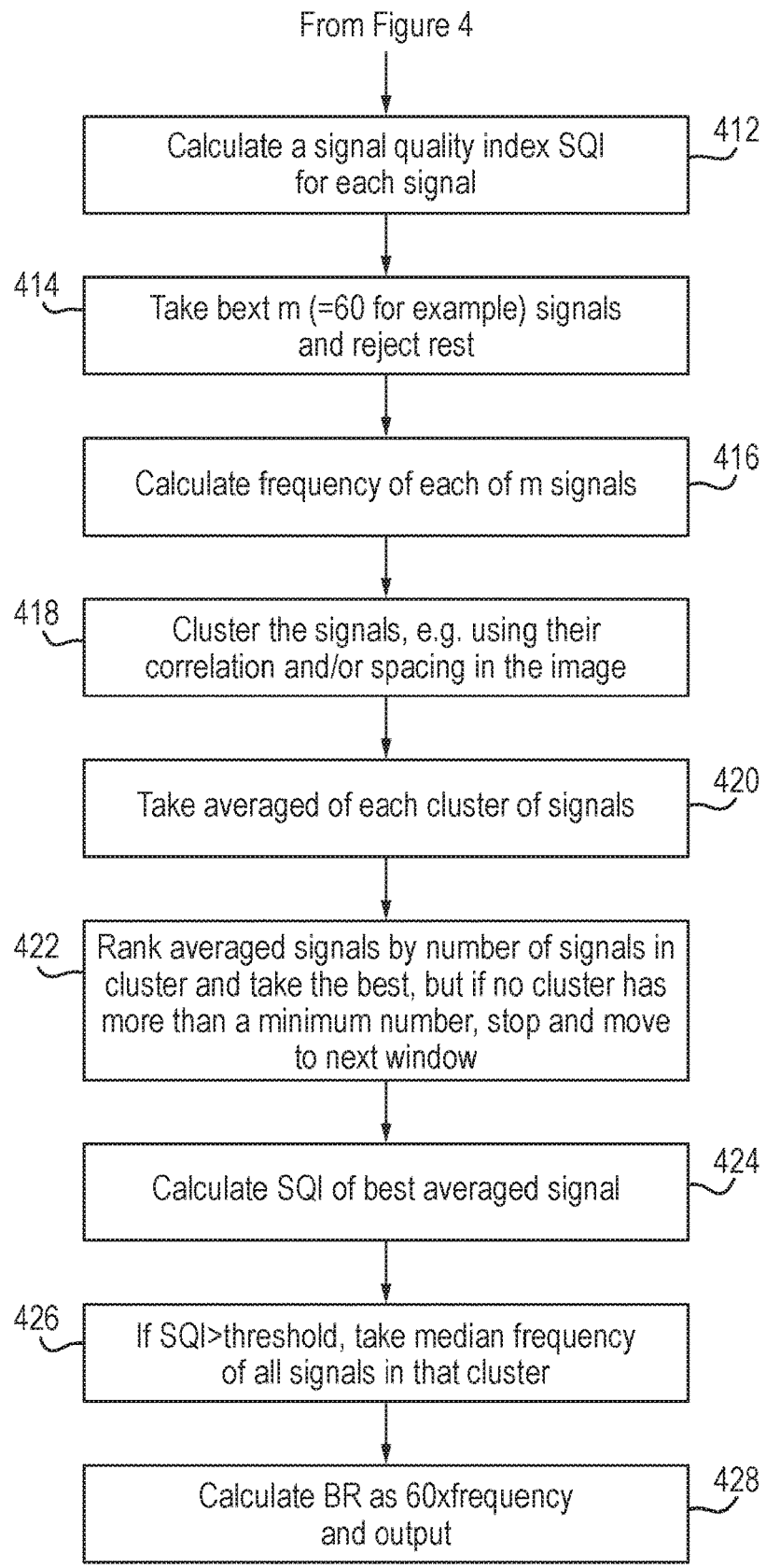

METHOD AND APPARATUS FOR ESTIMATING BREATHING RATE

CROSS-REFERENCE TO RELATED APPLICATIONS

This application is a 371 U.S. National Stage of International Application No. PCT/GB2017/050128, filed Jan. 19, 2017, which claims priority to British Patent Application No. 1601142.1, filed Jan. 21, 2016. The entire disclosures of the above applications are incorporated herein by reference.

The present invention relates to a method and apparatus for estimating the breathing rate of a respiring subject from a video image of the subject.

Many techniques have been developed over recent years for obtaining an estimate of the breathing rate of a respiring subject which are less intrusive than traditional contact techniques such as impedance pneumography. For example, the breathing rate can be estimated from respiratory modulation of the heart rate as detected in an electrocardiograph (ECG) or photoplethysmogram (PPG) signal or respiratory modulation of the amplitude of a PPG signal. Further, in recent times, techniques have been developed for obtaining a breathing rate signal from a video image of subject either by detecting a PPG signal in the image or by detecting respiration movement, see for example Wim Verkruysse, Remote plethysmographic imaging using ambient light, Tarassenko et al, Non-contact video-based vital sign monitoring using ambient light and auto-regressive models and Wu, H.-y., Rubinstein, M., Shih, E., and Freeman, W., 2012. Eulerian Video Magnification for Revealing Subtle Changes in the World.

Many of these techniques are suitable for use in relatively controlled clinical settings, however it would be useful to be able to detect the breathing of respiring subjects in a wider variety of settings including security applications, fitness, health and well-being in the home or elsewhere, where the subject or environment may be less controlled. For example, being able to monitor a subject in a room, such as a secure room in a detention facility e.g. a prison or police cell, a room in a hospital or care home, or even room in the home, workplace or leisure facility such as a gym, but able to freely move within the room would be useful, but is much more difficult. In real life subjects mix periods of high activity and large movement with periods of relative immobility (seated or lying), will in general be clothed and have bedding to cover themselves. Periods of inactivity while lying down, may coincide with the subject covering themselves partly or completely (known as "tenting") with bedding. Further, within rooms lighting conditions can vary with time, sometimes rapidly. Secure rooms are sometimes lit with visible artificial light and are sometimes completely dark with infrared being the only illumination available. The conventional video sensors are also quite noisy. Similar problems of movement and variable illumination occur also in fields such as fitness and health and well-being in the home or elsewhere.

Thus in a video of such an environment there may be many signals that might be breathing rate. Even movements that are caused by the subject breathing in general will not be in the same direction. Also even if the true breathing rate is the strongest signal in the room, it can be perturbed by the aforementioned environmental factors, or by the subject's irregular breathing, making it hard to be certain that it is the desired signal.

Many of the prior art proposals for detecting breathing in video images are actually based on careful control of the subject being monitored and the lighting conditions in the environment. Thus although they claim success in detecting breathing and estimating breathing rate, in general the subjects were required to remain relatively still and to breathe evenly, the subjects were not obscured and the lighting conditions were kept relatively constant. Monitoring a freely-moving subject within a room is, in practice, much more difficult. Existing systems do not provide vital signs monitoring or breathing rate detection which can operate reliably in the face of these difficulties. Being able to detect the breathing rate of a subject in these less controlled conditions would significantly improve the ability to monitor the well-being of such a subject and to comply with a duty of care requirement.

The present invention provides a method and apparatus for estimating the breathing rate of a respiring subject in a room from a video image of the whole room which can reliably provide a breathing rate estimate, or indicate that no breathing is detected, despite the difficulties mentioned above. In particular breathing rate can be estimated whether the subject is covered or uncovered or in any stationary body pose.

SUMMARY OF THE INVENTION

A first aspect of the present invention provides a method of obtaining an estimate of the breathing rate of a respiring subject in a room from a video image frame sequence of the room, the method comprising the steps of:

detecting and tracking image feature points in the video image frame sequence;

taking the values of the spatial coordinates of each of said tracked feature points in each frame of the video image frame sequence as time series signals;

selecting those time series signals which correlate most strongly with each other;

calculating the principal components of the selected time series signals;

calculating the frequency of at least one of the principal components; and outputting an estimate of breathing rate corresponding to said frequency.

Forming time series signals from the frame coordinates of the tracked features can provide two time-series signals for each feature point—one of the x-coordinates and one of the y-coordinates, or one time series for each feature point, e.g. the two coordinates can be combined, for example by applying principal component analysis to the x- and y-signals and taking the component with the largest eigenvalue.

An advantage of selecting time series signals which correlate most strongly with each other is that it is a lot more sensitive to tiny movements that result in many tracks that only weakly correlate with the true breathing rate. This correlation step is not dependent on the breathing signal having a strong signal/noise ratio, and so would perform better when the subject is, for instance, covered—e.g. under a thick duvet.

The method may further comprise the step of selecting feature points based upon at least one of: their spacing across the image, and their strength as returned by the feature point detecting algorithm. It may also comprise the step of discarding the weaker of any two selected feature points whose spacing in a frame of the video sequence is below a predetermined spacing threshold.

The step of selecting those time series signals which correlate most strongly with each other may comprise forming a matrix of pair-wise signal correlations, effectively a similarity matrix, and multiplying the matrix by itself m times (raising it to the power m) to form amplified correlation values, summing for each signal its amplified correlation values and selecting a plurality of the signals with the highest summed amplified correlation values. The advantage of raising the matrix to the mth power is that it amplifies the connectedness of a signal that belongs to a "clique" of inter-correlated signals, and weakens the connectedness scores of signals that do not belong to such cliques.

The step of selecting the plurality of the signals may comprise selecting those with a summed amplified correlation above a predetermined threshold. The threshold may be calculated based on the median and highest summed amplified correlation values on the mean/standard deviation of the correlation values, or on the highest/lowest correlation values, or similarly. It will be set to achieve the desired result on examples of test video sequences.

Preferably the time series signals are pre-processed by de-trending, change reducing to attenuate large changes in the signal, and low pass filtering them, and preferably they are differentiated before their correlation is calculated. The advantage of this is that because it reduces the impact of non-linear trends on the correlation. Non-linear trends in the signal tend to arise because on low-contrast surfaces without sharp corners (e.g. bed sheets) feature points can sometimes "wander" noisily.

The step of calculating the frequency of at least one of the principal components may comprise taking the first n principal components, where n is an integer between 1 and 10, preferably 3-8, more preferably 5, calculating a signal quality index of each of the n components, and selecting the best quality component for the steps of calculating its frequency and outputting a breathing rate estimate.

Preferably several signal quality indexes are calculated for each component, a first representing extremum (e.g. peak or trough) consistency, a second representing the correlation between the component and the selected signals, and a third representing the spacing of the feature points contributing to this component. The spacing-related signal quality index ensures that all the signals that are correlated with a component have to be tightly spatially grouped in the video image (calculate the average pairwise distance between the feature point tracks that the signals originated from, and ensure it is below a manually set distance threshold). Preferably the frequency of the component has to be above a minimum cutoff (7.5 bpm). This is because for certain window sizes (20 seconds) the peak consistency SQI becomes particularly unreliable for frequencies less than 7.5 bpm.

Preferably feature points which do not persist in the video image sequence for more than a preset number of frames, e.g. the whole time window being processed, are discarded. Avoiding using incomplete tracks improves the quality of the results.

One embodiment of the invention provides a method and apparatus for extracting a breathing rate estimate from video images of a respiring subject. Signals corresponding to the spatial coordinates of feature points tracked through the video sequence are de-trended and excessively large changes are attenuated to reduce movement artefacts. The signals are differentiated and signals which correlate most strongly with other signals are selected. The selected signals are subject to principal component analysis and the best quality of the top five principal components is selected, assuming its signal quality is above a predetermined threshold, and its frequency is used to calculate and output a breathing rate estimate. If no principal component is above the signal quality threshold(s), then a breathing rate estimate is not output. Knowing when to output an estimate and when not to output an estimate is highly advantageous when processing video images of whole rooms as there may be many periodic signals not relating to breathing, such as other repetitive movements—e.g. foot tapping, rocking, fidgeting, walking and so on. The method is particularly suitable for detecting respiration in subject in secure rooms where the video image is of substantially the whole room and the subject is only a small part of the image, and maybe covered or uncovered. The step of attenuating the signals may involve comparing frames separated by one 0.1 to 0.5 seconds or 0.2 to 0.3 seconds, and reducing signal amplitudes above a predetermined maximum to the predetermined maximum. This is preferably conducted on the differential signals, and the attenuated differential signals are then reintegrated.

Another embodiment of the invention provides a method and apparatus for extracting a breathing rate estimate from video images of a respiring subject. Signals corresponding to the spatial coordinates of feature points tracked through the video sequence are filtered and excessively large changes are attenuated to reduce movement artefacts. The most suitable signals according to a signal quality index favouring strong periodicity are selected and similar signals are clustered. The largest cluster of signals which have a good quality signal index are selected and the frequency of each of the signals in the cluster is calculated, for example using peak counting. The median frequency of the signals in the selected cluster is output as the breathing rate estimate. The method is also suitable for detecting respiration in subject in secure rooms where the video image is of substantially the whole room and the subject is only a small part of the image, and maybe covered or uncovered.

The invention will be further described by way of non-limitative example, with reference to the accompanying drawings in which:—

FIG. 1 schematically illustrates a subject in a secure room and an apparatus in accordance with one embodiment of the invention;

FIG. 2 schematically illustrates example frames from a video image frame sequence;

FIG. 3 schematically illustrates signals extracted from a video image frame sequence;

FIG. 6 is a flowchart illustrating an alternative embodiment of the invention;

Figure 7A:
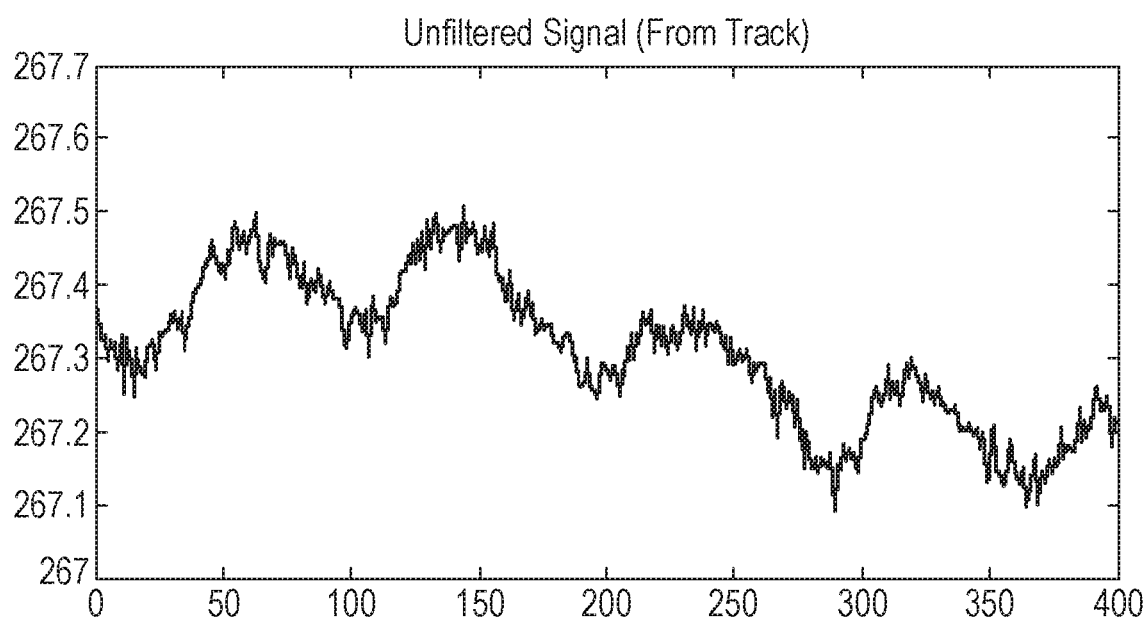
Figure 7B:
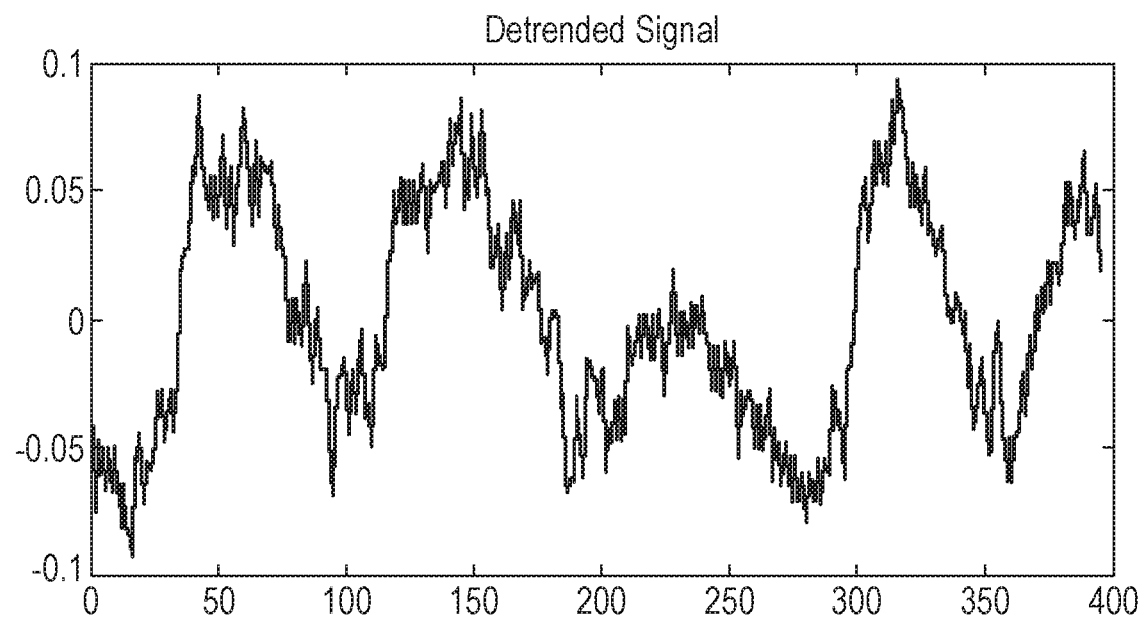
Figure 7C:
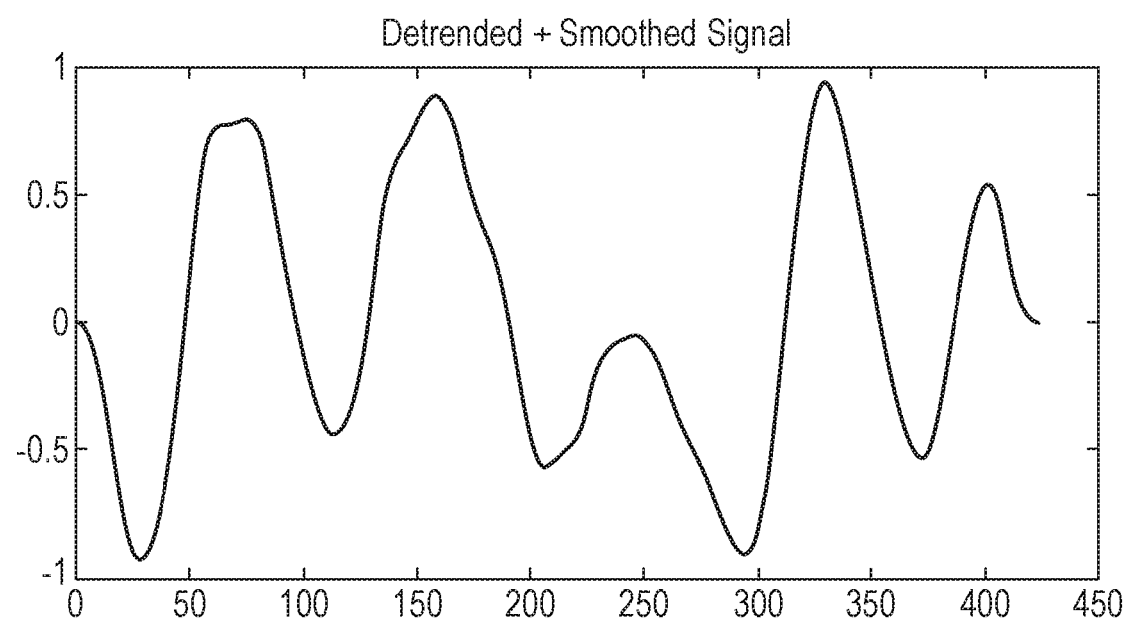
Figure 7D:
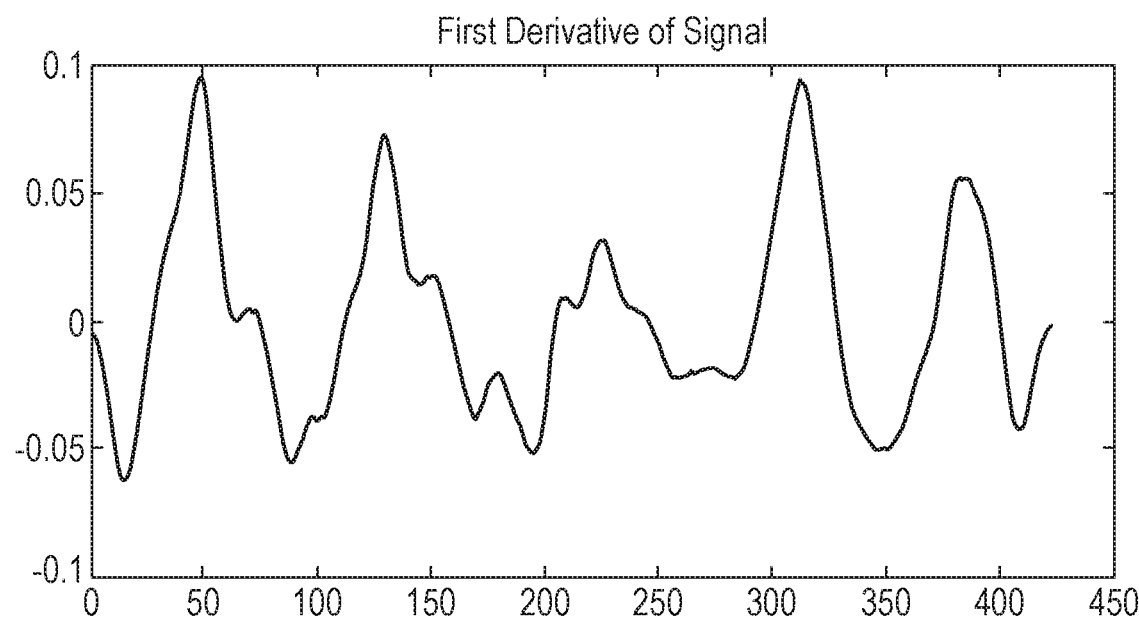
Figure 7E:
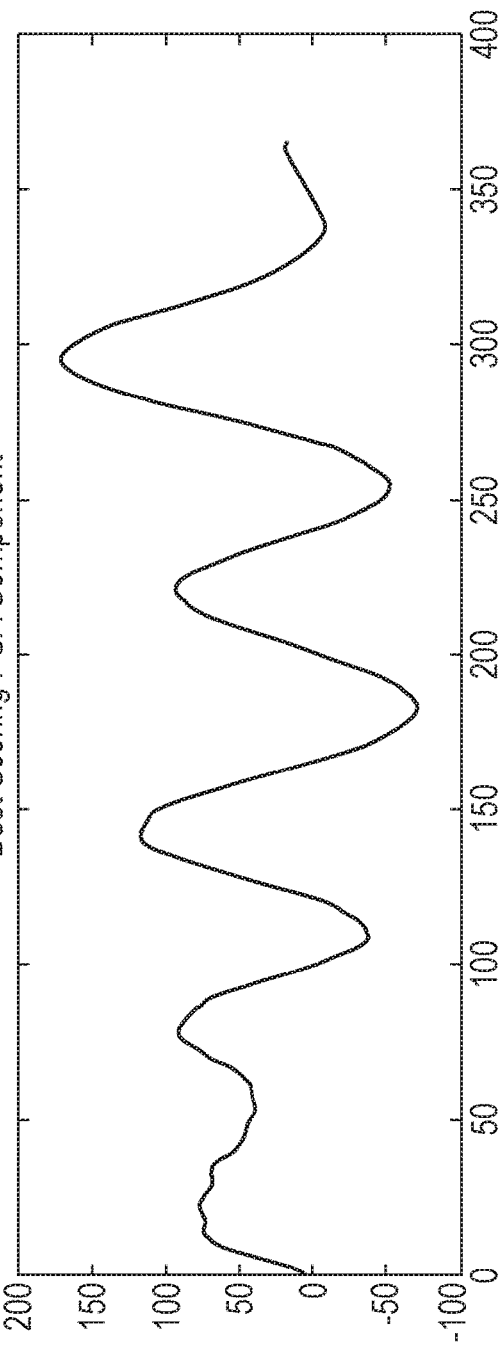
Figure 7F:
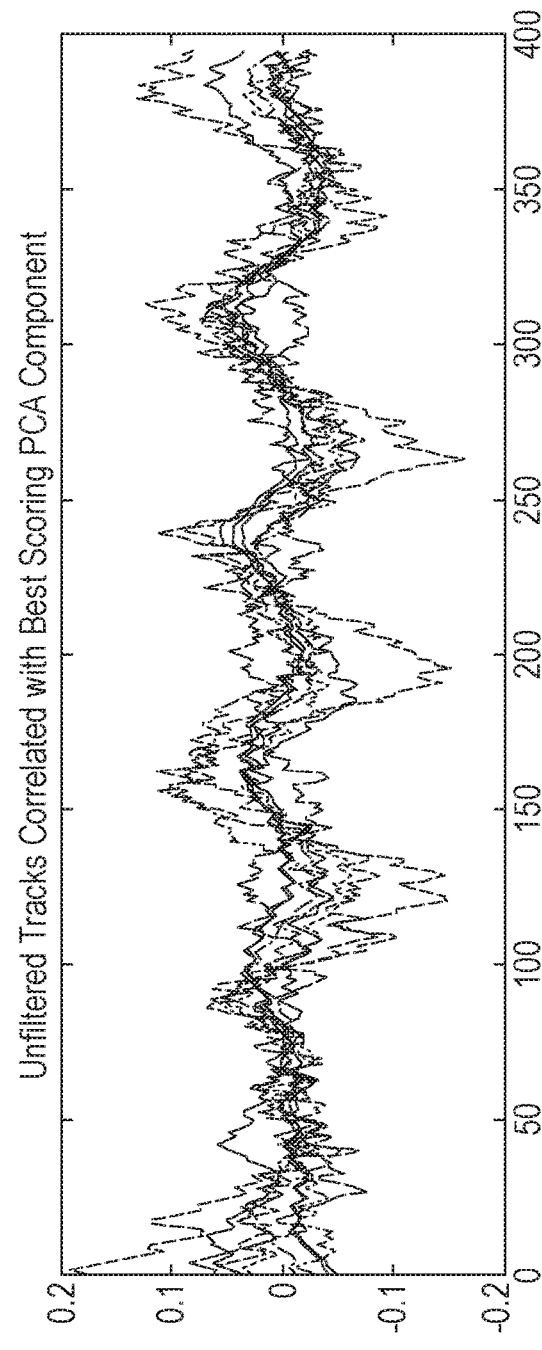
Figure 8:
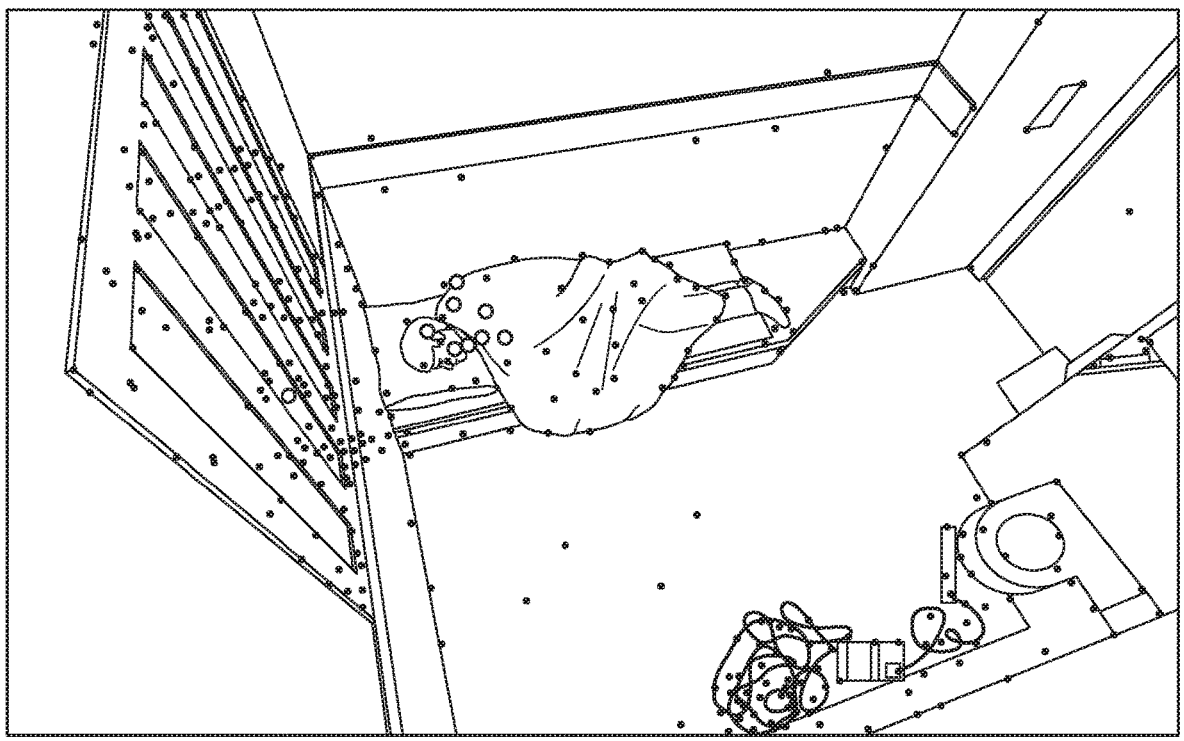

FIG. 7 (A) to (F) illustrate an example signal and its processing according to an embodiment of the invention;

FIG. 8 is a frame of a video sequence to which an embodiment of the invention has been applied to produce the signal of FIG. 7

An embodiment of the invention will now be described with reference to its application to monitoring of a subject in a secure room such as a prison cell or police cell although it should be understood that the method and apparatus are applicable in other applications such as clinical applications in hospitals or health and wellbeing applications such as gyms and health facilities, or to monitoring in the home.

Figure 1:
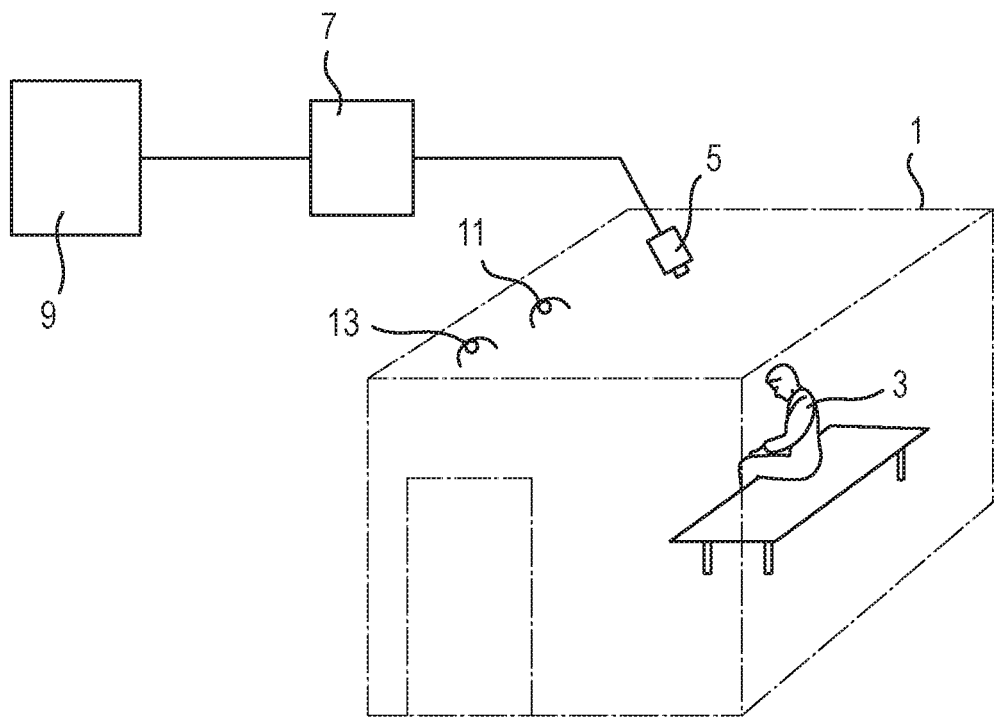

FIG. 1 schematically illustrates a secure room 1 occupied by a respiring subject 3 who is monitored by a video camera 5 and is illuminated selectively by visible spectrum artificial lighting 11 or infrared lighting 13. The output from the video camera is a conventional digital video output consisting of a series of image frames, typically at twenty frames per second, with red, green, blue and infrared intensities across the image as pixel values forming each frame. The video signal is processed by a signal processor 7 and the results are displayed on a display 9. The results may be an estimate of the breathing rate, or an indication that no breathing can be detected, together with an indication of the length of time for which no breathing was detected. The signal processor 7 may be a dedicated signal processor or a programmed general purpose computer. The display 9 may display the video image, as well as other information such as other vital signs data.

This embodiment of the invention is based on detecting breathing by tracking periodic movement in the video image of the room. Thus the video camera 5 provides an image not only of the subject, but also of the room. By detecting periodic movement in the expected physiological range for breathing and measuring the frequency of this periodic movement, an estimate of breathing rate can be obtained and displayed on display 9. The periodic movement may be movement of parts of the body of the subject 3, movement of articles associated with or in contact with the subject such as clothing or bedding, or manifested as periodic changes in intensity in certain regions in the image.

Figure 4:
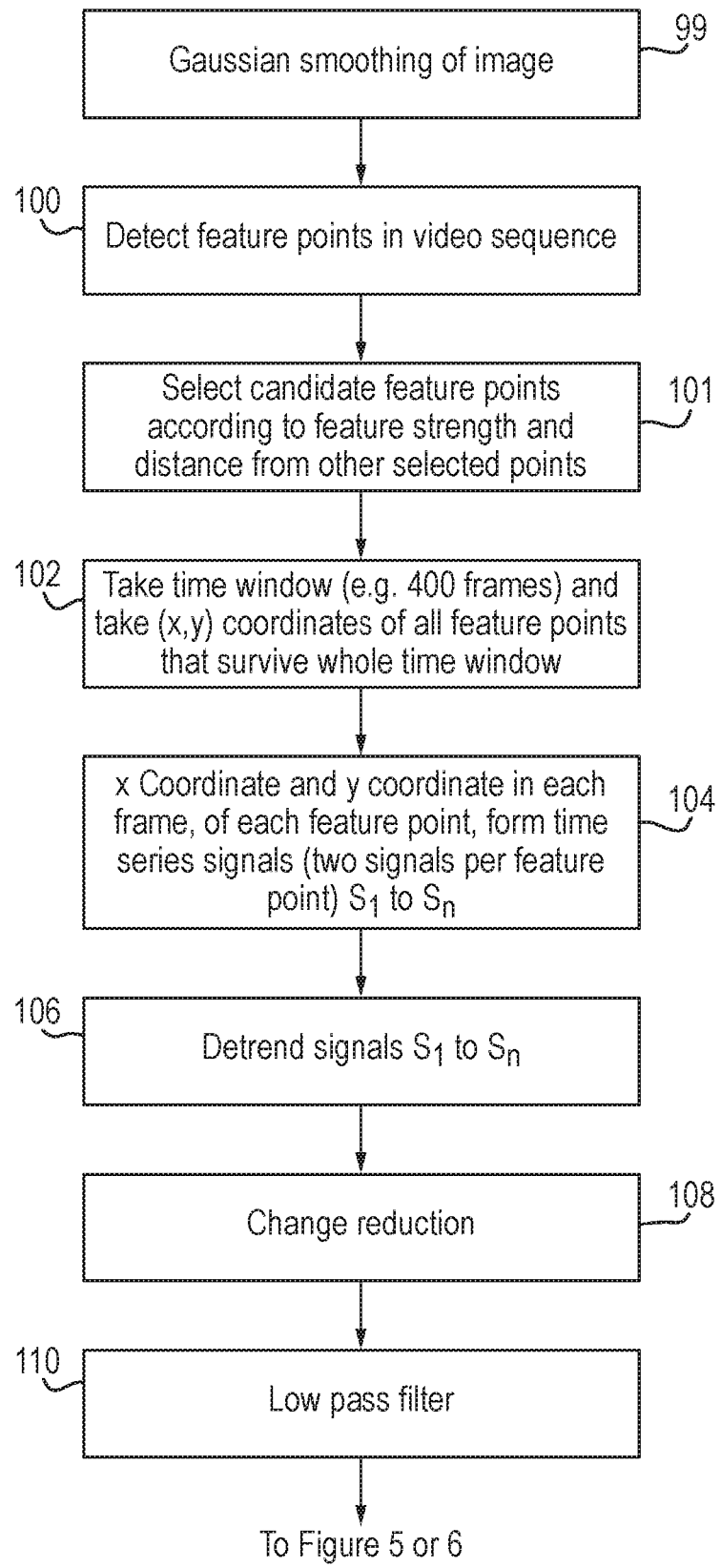
FIG. 4 is a flow diagram explaining the signal processing in accordance with one embodiment of the invention.

As illustrated in FIG. 4, in a first step 99 the image is smoothed—e.g. using Gaussian smoothing and then in step 100 feature points in the video sequence are detected. This may be conducted on a grayscale image formed from the RGB channels, e.g. by averaging them. There are many ways of detecting feature points in a video sequence using off-the-shelf video processing algorithms. For example, feature points consisting of recognisable geometrical shapes such as corners or edges can be detected based, for example, on the gradient of intensity variation in one or two dimensions and any such algorithm which identifies image feature points can be used in this invention. A feature point detecting and tracking algorithm usable with this invention is KLT tracking looking for Harris features, SIFT features, ORB/SURF features.

Most feature point detecting algorithms will generate many more candidate feature points than are required. For the purposes of the present invention the feature points are preferred which are strong and relatively evenly spaced. This is achieved in an iterative process in step 101 by selecting feature points found by the feature point detecting algorithm based on two metrics: one based on the strength of the point as measured and output by the feature point detecting algorithm (the strength might be, for example the intensity gradient, but all algorithms output some measure of strength), and one which is the distance to already selected feature points. Thus a first feature point from those generated by the feature point detecting algorithm is selected, e.g. the strongest, and then the distance from all other feature points to the selected feature point is measured. A weighted combination of each feature point's strength and distance to the already selected point is found, and the one with the highest value is selected. The minimum distances of the remaining feature points to the closest of the two already selected feature points are recalculated, the weighted combination of strength and minimum distance recalculated, and the feature point with the highest value is selected. This process of calculating distances to the closest of the already selected feature points and selecting the one with the highest combination of strength and distance continues until the desired number of feature points, e.g 200 has been selected. This process of selecting feature points can be repeated any time the number of feature points falls below a desired value as a result of some subsequent step.

Figure 2:
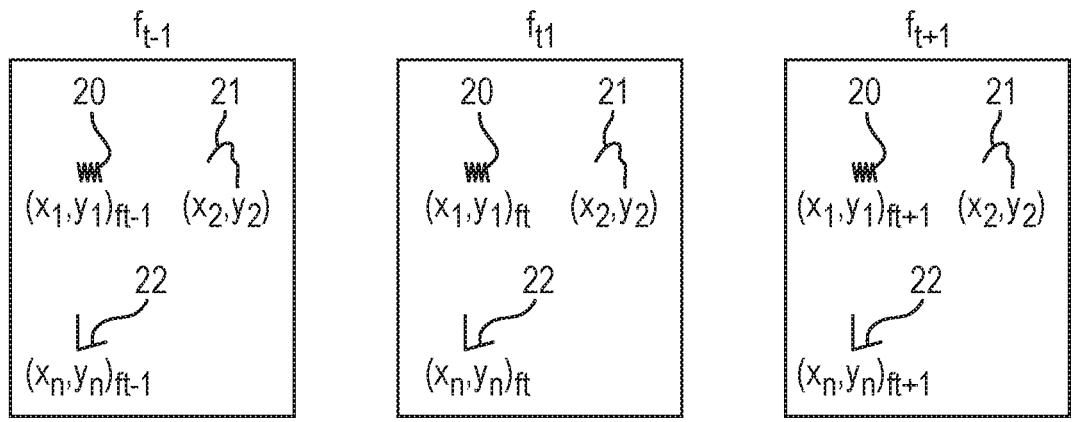

In step 102 a sequence of video frames is taken for processing as a batch, such as four hundred frames (corresponding to twenty seconds of video at a conventional frame rate of twenty frames per second). The x coordinates and y coordinates of all of the selected feature points that are present in all one four hundred frames of the sequence are then taken. The variation in x coordinate or y coordinate of each feature point through the frame sequence is then taken as a signal (which may or may not include a breathing movement component) to be processed. Thus step 104 will output n signals where n is twice the number of feature points tracked. FIG. 2 illustrates schematically three frames of a video image frame sequence, the frames being at t−1, t and t+1, with a number of detected feature points 20, 21, 22 in them. Each detected feature 20, 21, 22 point will contribute an x, y coordinate pair and the variation of the x and y coordinate of each of these pairs through the sequence (i.e. as a function of time) is taken as a signal. FIG. 7(A) shows a single example signal from a video sequence of which FIG. 8 is a single frame with points which are the sources of these signals marked as dots.

In step 106 the n signals are de-trended, e.g. by subtracting the best-fit line through the data (best-fit calculated for example by least squares), resulting in a signal such as that shown in FIG. 7(B), and in step 108 a change reduction process is applied to attenuate excessively large movements and thus reduce movement artefacts. As an example the frame to frame differences in the signals can be calculated and any change which is larger than three times the first to third interquartile range is reduced to three times the interquartile range. An example of an algorithm to achieve this is:

Calculate the frame-to-frame differences of the signal (i.e. calculate the first derivative of the signal)

Sort the frame-to-frame differences in order of magnitude

Find the first and third quartile of this sorted range (25% largest, 75% largest)

Calculate the difference between the first and third quartile, and multiply by a given constant (chosen empirically)—this is the "scaled inter-quartile range"

For every frame-to-frame difference, if the absolute difference (irrespective of sign) is greater than the scaled inter-quartile range, then reduce it to the scaled inter-quartile range.

Reintegrate the signal (by calculating the cumulative sum of the frame-to-frame differences).

In this process the frame-to-frame differences can be calculated between adjacent frames, or between pairs of frames separated by a short time, e.g. from 2 to 10 frames apart (to achieve 0.1 to 0.5 seconds spacing), more preferably 4-6 frames apart (to achieve 0.2 to 0.3 second spacing).

Optionally the signal is then normalised to a zero mean and standard deviation of one by standard signal processing techniques. In step 110 a low pass filter is applied to the signals, such as Gaussian smoothing, for example with a pass band of zero to thirty breaths per minute (0-0.5 Hz). FIG. 7(C) shows the signal of FIG. 7(A) after this detrending and smoothing processing.

Figure 5:
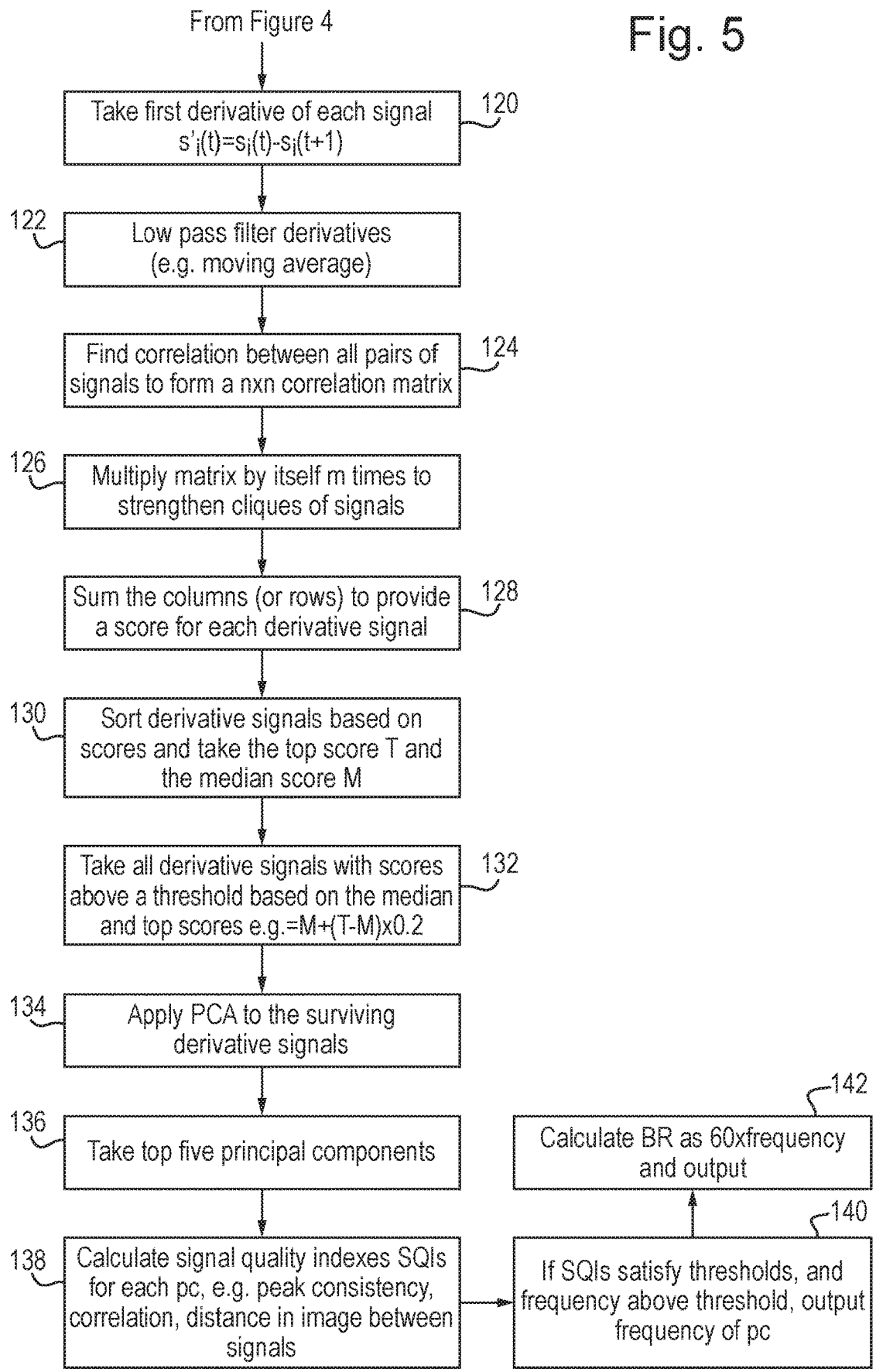
FIG. 5 is a continuation of the flowchart of FIG. 4.

FIG. 5 shows the subsequent processing according to a first embodiment.

In step 120, the first derivative of each of the signals $S_1$ to $S_n$ is taken. This is simply a matter of subtracting the value of the signal at each time point from the value at the preceding time point. FIG. 7(D) shows the first derivative of the de-trended and smoothed signal of FIG. 7(C). Subsequent processing in FIG. 5 occurs on the derivative signals. In step 122 the derivative signals are low passed filtered, e.g.

by calculating a moving average, and then in step 124 the absolute Pearson correlations $c_{ii}$ (i=1 to n) between all pairs of derivative signals $S_1'$ to $S_n'$ is calculated, these correlations forming an n×n correlation matrix.

$$C = \begin{pmatrix} c_{11} & \cdots & c_{1n} \\ \vdots & \ddots & \vdots \\ c_{n1} & \cdots & c_{nn} \end{pmatrix}$$

Each element in the matrix represents the correlation between two derivative signals. In step 126 the matrix is multiplied by itself in a matrix product m times (m=between 4 and 128) to strengthen "cliques" of derivative signals. A clique is a group or cluster of derivative signals that all correlate well with each other. This is effectively raising the matrix to the $m^{th}$ power and as a result the high correlations are increased compared to the rest.

$$\begin{pmatrix} c_{11} & \cdots & c_{1n} \\ \vdots & \ddots & \vdots \\ c_{n1} & \cdots & c_{nn} \end{pmatrix} \cdot \begin{pmatrix} c_{11} & \cdots & c_{1n} \\ \vdots & \ddots & \vdots \\ c_{n1} & \cdots & c_{nn} \end{pmatrix} \cdot \begin{pmatrix} c_{11} & \cdots & c_{1n} \\ \vdots & \ddots & \vdots \\ c_{n1} & \cdots & c_{nn} \end{pmatrix} \cdots = C^m$$

The parameter m is used to tune the algorithm and its value is selected to achieve the desired quality of results within a reasonable time. A higher m is generally better but results in higher computation times. It is tuned by running the algorithm with different values of m on a number of test video sequences and observing the results. Typically values of m between 10 and 50 give a reasonable balance of quality and computation speed.

In step 128, a score for each derivative signal is found by summing either the row values or column values (they are the same) which can be achieved by multiplying the matrix Cm by a unit column or row vector of size n.

The derivative signals are then sorted based on these scores in step 130 and the top score and medium score are noted. A threshold is calculated in step 132 from the median score and top score, for example the threshold equals M+(T−M)×0.2, and then in step 134 principal component analysis is applied to the surviving derivative signals. In step 136 the top five principal components are taken and three signal quality indices SQI1, SQI2 and SQI3 are calculated for each principal component in step 138.

For example, one signal quality index SQI1 can be a measure of the extrema (peaks and/or troughs) consistency. One way of forming such a measure is to:
  Perform extrema finding on the signal to find all peaks/troughs (using a standard technique).
  Find the distances between all adjacent peaks/troughs
  Calculate the Coefficient of Variation (defined as standard deviation divided by the mean) of these distances—this is the peak consistency (smaller values indicate better peak consistency)
  Signals with fewer than 5 peaks+troughs are discarded (given an infinite peak consistency)

A second signal quality index SQI2 can be obtained by calculating the correlation between each principal component and the surviving derivative signals from step 134 and counting how many are above a predetermined correlation threshold. FIG. 7(F) shows the constituent signals which are similar in frequency and phase to the best-scoring PCA component representing the breathing rate for the signals from the video sequence of which FIG. 8 is a frame. In FIG. 8 the locations from which these components originate are marked differently from the other dots—they are around the head and shoulders of the subject, with one on the wall of the room being caused by a reflection.

A third signal quality index SQI3 is the average pair-wise distance between all the derivative signals that correlate well (i.e. above a predetermined threshold) with the principal component. The aim is to select signals that correlate well and are from the same region in the image.

Having obtained the signal quality indexes for each principal component, in step 140 whichever principal component has signal quality indexes above a threshold (or if more than one satisfies this requirement, then the principal component which also has the best signal quality measured by one SQI or a combination of SQIs) is taken and its frequency calculated. The frequency can be calculated by peak counting or by spectral analysis (e.g. FFT). If the frequency is above 0.125 Hz (7.5 breaths per minute) this frequency is used to output in step 142 an estimate of the breathing rate, for example if the breathing rate is required in breaths per minute and the frequency is in Hertz, the breathing rate estimate is sixty times the frequency. FIG. 7(E) shows the best-scoring PCA component from signals derived from the video sequence of which FIG. 8 is a single frame.

Figure 3:
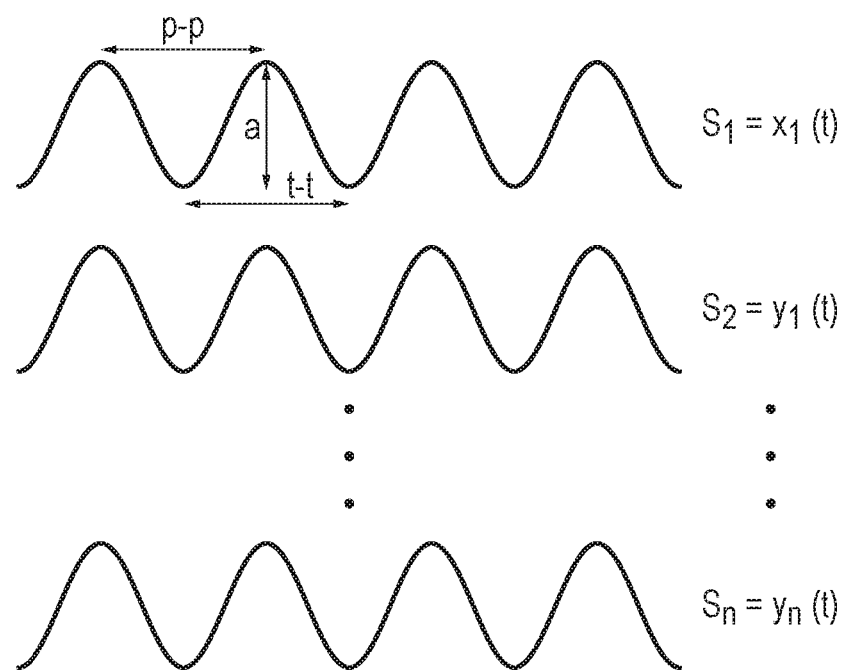

FIG. 6 shows an alternative process to that of FIG. 5, this being a second embodiment of the invention. In steps 412 and 414 the subset of the signals which have the best signal quality are selected. A variety of signal quality measures are usable as above. These may be measures of its periodicity, its overall amplitude (how much the tracks move), the power ratio between certain frequency bands of the signal, and the amplitude consistency For example, suitable signal quality indexes are obtained by measuring the peak, trough and amplitude consistencies, e.g. by measuring peak to peak times in each signal, taking the standard deviation and the natural log of the standard deviation, measuring the trough to trough times and taking the natural log of the standard deviation of the trough to tough to trough times and measuring the amplitude of each cycle of the signal and taking the natural log of the standard deviation of the amplitudes, these quantities being illustrated in the signal $S_1$ of FIG. 3. In this embodiment a signal quality index (SQI) is calculated which is log $SD_{amplitude}$+max of (log $SD_{pp}$ or log $SD_{tt}$).

The signals are then ranked according to the signal quality index and in step 414 a subset of them which have the best SQI are taken, for example the best m=60 signals are taken, and the rest are rejected. If there are insufficient signals with a signal quality index above a preset threshold, then the process stops and no breathing rate estimate is output for this subject of video frames. In that case, the next batch of video frames, for example, a batch of four hundred frames starting one second after the start of the preceding batch would be taken and processed. If no breathing rate estimate is output after a pre-set number of seconds, an alarm may be generated and displayed on display 9.

Assuming that there are a sufficient number of signals with a satisfactory signal quality index, in step 416 the frequency of each of the signals is calculated, for example by using the peak to peak and trough to trough times and averaging them or by looking for the frequency which has the strongest peak in a power spectrum (e.g. FFT) of the signal.

Although a breathing rate estimate could be calculated by, for example, averaging these frequencies from the sixty signals, in the present embodiment further processing is conducted to increase the chances that the periodic signal being detected is a breathing rate signal. This is achieved by clustering similar signals and then taking the largest cluster which has good signal quality index. In more detail, in step 418 the signals are clustered, for example using the magnitude of the Pearson correlation and preferably also by examining the distance between the feature points in the image and clustering signals which come from feature points that are close together. It should be noted that for detecting breathing movement, signals may be in phase or antiphase, which is why the magnitude of the correlation is used. Thus in the clustering process, random pairs of signals are taken and compared to each other with the two being formed into a cluster if the magnitude of their correlation is above a threshold and if they originate from feature points which are not spaced by more than a certain amount. [I think we probably need to give examples of the thresholds and how this is done in more detail]. When two signals are to be clustered, they are averaged together to provide an average signal which is then compared to other signals as the clustering process continues.

This will generally result in a relatively small number of signal clusters, with each cluster including a different number of signals. In step 420, the signals within each cluster are averaged together and in step 422 the average signals are ranked by the number of signals from their cluster and, assuming that at least one cluster has more than a minimum number of signals, the averaged signal from the largest cluster is taken and in step 424, its signal quality index is recalculated. The signal quality index may be the same as the signal quality index used in step 412, or maybe a different signal quality index. In step 426 if the signal quality index of the averaged signal from the largest cluster is above a pre-set threshold, the median frequency of all of the signals in that cluster is calculated and in step 428 this frequency is used to output an estimate of the breathing rate. For example, if the breathing rate is required in breaths per minute and the frequency is in Hertz, the breathing rate estimate is sixty times the median frequency.

Having output a breathing rate estimate, by either the process of FIG. 5 or FIG. 6, the process repeats on the next batch of video frames. Preferably the batches are frames from overlapping time windows, moved along by a time increment such as one second which, with a twenty second window length, implies an overlap of nineteen seconds. However, different length time windows and different overlaps may be selected as desired.

The video camera 5 is capable of recording video under natural light or infrared light and the method of the invention is effective in detecting respiration signals in both types of video image. The invention can also detect respiration whether the subject is covered or uncovered and in any position within the video image.

The invention may be embodied in a signal processing method, or in a signal processing apparatus which may be constructed as dedicated hardware or by means of a programmed general purpose computer or programmable digital signal processor. The invention also extends to a computer program for executing the method.

The invention claimed is:

1. A method of obtaining an estimate of a breathing rate of a respiring subject in a room from a video image frame sequence of the room, the method comprising the steps of:
   detecting and tracking image feature points in the video image frame sequence, wherein feature points which do not persist in the video image frame sequence for more than a preset number of frames are discarded;
   taking values of spatial coordinates of each of the tracked feature points in each frame of the video image frame sequence as time series signals;
   calculating correlations between the time series signals;
   selecting, on the basis of the calculated correlations between the time series signals, those time series signals which correlate most strongly with each other;
   calculating principal components of the selected time series signals;
   calculating a frequency of at least one of the principal components; and
   outputting an estimate of breathing rate corresponding to the frequency.

2. The method according to claim 1, wherein the step of selecting those time series signals which correlate most strongly with each other comprises forming a matrix of pair-wise signal correlations and multiplying the matrix by itself to form amplified correlation values, summing for each signal its amplified correlation values and selecting a plurality of the signals with the highest summed amplified correlation values.

3. The method according to claim 2, wherein the step of selecting a plurality of the signals comprises selecting those with a summed amplified correlation above a first threshold.

4. The method according to claim 1, further comprising the step of selecting feature points based upon at least one of: their spacing across the image and their strength.

5. The method according to claim 4, further comprising the step of discarding the weaker of any two selected feature points whose spacing in a frame of the video sequence is below a predetermined spacing threshold.

6. The method according to claim 1, wherein the time series signals are differentiated before their correlation is calculated.

7. The method according to claim 1, wherein the step of calculating the frequency of at least one of the principal components comprises taking a first n principal components, where n is an integer between 4 and 10, calculating at least one signal quality index of each of the first n principal components, and selecting the best quality component for the steps of calculating its frequency and outputting a breathing rate estimate.

8. The method according to claim 7, wherein at least one of the following signal quality indexes is calculated for each component, a first signal quality index representing extremum consistency, a second signal quality index representing the correlation between the component and the selected signals, a third signal quality index representing a distance in the video image between the tracked feature points corresponding to the signals.

9. The method according to claim 8, wherein the step of selecting the best quality component comprises selecting a component with one or a combination of: an extremum consistency above a predetermined consistency threshold, a correlation between the component and the selected signals above a predetermined correlation threshold, the distance in the video image between the tracked feature points corresponding to the signals below a predetermined distance threshold.

10. The method according to claim 1, further comprising the step of attenuating the signals by comparing frames separated by one of the ranges: 0.1 to 0.5 seconds, 0.2 to 0.3 seconds, and reducing signal amplitudes above a predetermined maximum to the predetermined maximum.

11. An apparatus for estimating a breathing rate of a respiring subject in a room from a video image frame sequence of the room, the apparatus comprising:

a video camera for capturing a video image sequence of the subject;

an image data processor configured to execute the steps of:

detecting and tracking image feature points in the video image frame sequence, wherein feature points which do not persist in the video image frame sequence for more than a preset number of frames are discarded;

taking values of spatial coordinates of each of the tracked feature points in each frame of the video image frame sequence as time series signals;

calculating correlations between the time series signals;

selecting, on the basis of the calculated correlations between the time series signals, those time series signals which correlate most strongly with each other;

calculating principal components of the selected time series signals;

calculating a frequency of at least one of the principal components; and outputting an estimate of breathing rate corresponding to the frequency; and a display for displaying the estimate of the breathing rate.

12. A computer program comprising program code means for executing on a computer system a method comprising the steps of:

detecting and tracking image feature points in a video image frame sequence, wherein feature points which do not persist in the video image frame sequence for more than a preset number of frames are discarded;

taking values of spatial coordinates of each of the tracked feature points in each frame of the video image frame sequence as time series signals;

calculating correlations between the time series signals;

selecting, on the basis of the calculated correlations between the time series signals, those time series signals which correlate most strongly with each other;

calculating principal components of the selected time series signals;

calculating a frequency of at least one of the principal components; and outputting an estimate of breathing rate corresponding to the frequency.

\* \* \* \* \*